United States Patent
Yamaguchi et al.

(10) Patent No.: US 7,763,846 B2
(45) Date of Patent: Jul. 27, 2010

(54) METHOD OF ANALYZING MASS ANALYSIS DATA AND APPARATUS FOR THE METHOD

(75) Inventors: Shinichi Yamaguchi, Kyoto (JP); Yusuke Inohana, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 683 days.

(21) Appl. No.: 11/783,467

(22) Filed: Apr. 10, 2007

(65) Prior Publication Data
US 2008/0067344 A1   Mar. 20, 2008

(30) Foreign Application Priority Data
Apr. 18, 2006   (JP) .............................. 2006-115031

(51) Int. Cl.
 *H01J 49/26*   (2006.01)
(52) U.S. Cl. ...................... 250/281; 250/282
(58) Field of Classification Search ................ 250/281, 250/282, 288, 286, 287; 702/23, 26, 27, 702/28, 19, 22, 24, 25, 29, 30, 31, 32
See application file for complete search history.

(56) References Cited

U.S. PATENT DOCUMENTS

| | | | | |
|---|---|---|---|---|
| 6,582,965 | B1 * | 6/2003 | Townsend et al. | 436/89 |
| 7,049,581 | B2 * | 5/2006 | Whitney et al. | 250/282 |
| 2002/0192708 | A1 * | 12/2002 | Steen et al. | 435/7.1 |
| 2006/0085142 | A1 * | 4/2006 | Mistrik | 702/27 |

FOREIGN PATENT DOCUMENTS

| | | |
|---|---|---|
| JP | 10-142196 A | 5/1998 |
| JP | 2001-249114 A | 9/2001 |

* cited by examiner

*Primary Examiner*—Jack I Berman
*Assistant Examiner*—Nicole Ippolito Rausch
(74) *Attorney, Agent, or Firm*—Westerman, Hattori, Daniels & Adrian, LLP

(57) ABSTRACT

The present invention provides a method and an apparatus for analyzing mass analysis data for easily deducing the structure of an unknown substance, based on data obtained by an $MS^n$ analysis. First, the structural formula of a precursor ion of the unknown substance is deduced based on the mass-to-charge ratio of the precursor ion (Step S12), and candidate structures which have the same compositional formula as the compositional formula deduced in Step S12, by combining the structure of the known substance and known structural change patterns (Step S14). Next, fragment ion peaks expected to appear from the candidate structures are deduced (Step S15), and based on the expected fragment ion peaks, the candidate structures are ranked in the order of probability (Step S16). Then, by comparing a mass spectrum of the known substance and that of the unknown substance, a common fragment ion peak is searched. (Step S19). If a common peak exists, assuming that a partial structure of the known substance corresponding to the peak is included also in the unknown substance, the candidate structures are narrowed down based on information on the partial structure (Step S21).

9 Claims, 3 Drawing Sheets

MS spectrum

MS² spectrum

MS spectrum

MS² spectrum

METHOD OF ANALYZING MASS ANALYSIS DATA AND APPARATUS FOR THE METHOD

The present invention relates to a method of analyzing mass analysis data for analyzing data obtained by an $MS^n$ analysis in which precursor ions originating from a sample to be analyzed are dissociated into fragment ions once or multiple times. More specifically, the invention relates to a method of deducing the structure of an unknown substance which is similar to a certain substance whose structure is known.

BACKGROUND OF THE INVENTION

An MS/MS analysis is a type of mass-analyzing method using an ion trap mass spectrometer or similar apparatuses. In a typical MS/MS analysis, an ion having a specific mass-to-charge ratio (m/z) is first separated from the material to be analyzed. This ion is called the precursor ion, or the parent ion. Next, the precursor ion thus separated is broken into fragment ions by a collision-induced dissociation (CID) process. Finally, as the dissociation mode varies depending on the structure of the precursor ion, the fragment ions produced by the dissociation process are subjected to a mass-analyzing process to obtain information about the mass and the chemical structure of the ion concerned.

In recent years, such apparatuses have been often used to analyze samples having larger molecular weights and more complex structures (or compositions) than in previous years. Some samples having special characteristics cannot be broken into ions having adequately small weights by a single dissociating step. One method for dealing with such a case is called the $MS^n$ analysis, in which the dissociating operation is repeated multiple (n−1) times and the fragment ions produced are subjected to a mass-analyzing process (refer to Patent Documents 1 and 2 for examples). If, as in the previous case, the dissociating operation is performed just once, the mass analysis of the fragment ions can be called the $MS^2$ analysis.

One popular analysis method for deducing the structure of an unknown substance based on data obtained by an $MS^n$ analysis is a so-called pattern matching method using a mass spectrum database. The mass spectrum database contains information on a variety of known compounds such as mass-spectral data obtained by a mass-analyzing process using a certain ionization method, names of compounds, molecular weights, compositional formulas, and structural formulas. By performing a pattern matching operation between a mass spectrum of a known compound and mass spectra of unknown compounds under a predetermined search condition, it is possible to identify the substance having a corresponding spectral peak pattern to that of the unknown substances.

[Patent Document 1] Japanese Unexamined Patent Application Publication No. H10-142196

[Patent Document 2] Japanese Unexamined Patent Application Publication No. 2001-249114

Even if such a database is large, not all compounds to be analyzed can be stored. In particular, it is practically impossible to register all the compounds of agrichemicals and/or pharmaceutical compounds to the database library, because many of them have an identical basic skeleton but have different substituted components or substituents (ethyl substitution for methyl, bromine substitution for chlorine for examples). Accordingly, if an unknown substance to be targeted is not registered in the database, it is difficult to deduce the molecular structure of the unknown substance.

To solve the above-described problem, the present invention intends to provide a method of analyzing mass analysis data for easily deducing the structure of an unknown substance based on data obtained by an $MS^n$ analysis.

SUMMARY OF THE INVENTION

Thus, a first aspect in accordance with the present invention provides a method of analyzing mass analysis data for deducing the structure of an unknown substance, based on the result of an $MS^n$ analysis in which a precursor ion originating from the unknown substance is dissociated into fragment ions by (n−1) steps (where $n \geq 2$) and then the fragment ions are subjected to a mass-analyzing process, the method comprising the steps of:

a) comparing the mass spectrum of the unknown substance obtained by the $MS^n$ analysis and the mass spectrum of a known substance similar to the unknown substance and then detecting a common fragment ion peak existing in both of the mass spectra;

b) identifying the partial structure of the known substance, the partial structure corresponding to the common fragment ion peak; and c) determining the partial structure as the partial structure of the unknown substance.

A second aspect in accordance with the present invention provides a method of analyzing mass analysis data for deducing the structure of an unknown substance, further comprising the steps of:

h) deducing the compositional formula of a precursor ion originating from the unknown substance based on the mass-to-charge ratio of the precursor ion;

i) creating candidate structures for obtaining the same compositional formula as the compositional formula deduced in step h), by combining the structure of the known substance and known structural change patterns;

j) deducing a fragment ion peak obtained by the $MS^n$ analysis of the candidate structures; and k) ranking the candidate structures in descending order of the probability of the structure of the unknown substance by comparing the fragment ion peak deduced in step j) and the fragment ion peak obtained by the $MS^n$ analysis of the unknown substance.

The present invention also provides an apparatus for analyzing mass analysis data for deducing the structure of an unknown substance, based on the result of an $MS^n$ analysis in which a precursor ion originating from the unknown substance is dissociated into fragment ions by (n−1) steps (where $n \geq 2$) and then the fragment ions are subjected to a mass-analyzing process, the apparatus comprising:

a) a measured data retriever for retrieving the mass spectrum of the unknown substance obtained by the $MS^n$ analysis;

b) a memory unit for storing (i) a mass spectrum of a known substance similar to the unknown substance, and (ii) partial structure information of the known substance, the partial structure corresponding to the detected fragment ion peak on the mass spectrum;

c) a common peak detector for comparing the mass spectrum of the unknown substance obtained by the measured data retriever and the mass spectrum of a known substance retrieved from the memory unit, and then detecting a common fragment ion peak existing in both of the mass spectra;

d) a partial structure retriever for retrieving the partial structure information corresponding to the common fragment ion peak from the memory unit; and e) a partial structure determining means for determining the partial structure as the partial structure of the unknown substance.

In the method of analyzing mass analysis data according to the first aspect of the present invention, the mass spectrum obtained by an MS$^n$ analysis of an unknown substance and the mass spectrum of a known substance which is similar to the unknown substance are compared, and then the structure of the unknown substance is deduced. Since a fragment ion peak originating from a known substance can be assigned to a partial structure of the known substance, by identifying a common fragment ion peak between the known substance and the unknown substance, it is possible to deduce the partial structure included in the unknown substance. Therefore, according to the method, it is easy to deduce the structure of a substance even if it is not registered in the database, thereby the analysis efficiency is improved. The "mass spectrum obtained by an MS$^n$ analysis of an unknown substance" can either be measured by a preliminary MS$^n$ analysis of the known substance or deduced based on the structure of the known substance.

In the first aspect of the present invention, it is preferable, when comparing the result of an MS$^n$ analysis of an unknown substance and the information on a known substance, to use a difference value between the mass-to-charge ratio of the precursor ion and the mass-to-charge ratio of the fragment ion at each step of the MS$^n$ analysis, in addition to the information on the fragment ion peak which was described earlier. In this case, a difference value between the mass-to-charge ratios such as described earlier is preliminarily calculated regarding the known substance, and then the difference value is compared with the difference value between the mass-to-charge ratios which is calculated from the result of the MS$^n$ analysis of the unknown substance. As a result of this comparison, a common difference value between them is detected. Since the difference value between the mass-to-charge ratios is attributable to an element desorbed by the dissociation of the precursor ion, and is attributable to a partial structure of the known substance, it is possible to deduce the partial structure included in the unknown substance by calculating the difference value between the mass-to-charge ratios obtained from both the known substance and the unknown substance. As a difference value between the mass-to-charge ratios, it is also preferable to use a difference value between a mass-to-charge ratio of a fragment ion at each dissociating step of the MS$^n$ analysis having multiple dissociation steps and a mass-to-charge ratio of a fragment ion or a precursor ion at the previous step, which were original ions of the fragment ion.

In the method of analyzing mass analysis data according to the second aspect of the present invention, it is possible to deduce the whole structure of an unknown substance, by combining the structure of a known substance which is similar to the unknown substance to be analyzed and known structural change patterns. It is likely that the structure of the unknown substance is almost the same as that of the known substance, with one or more different parts of the structure. Accordingly, the compositional formula of a precursor ion of the unknown substance is first deduced, and then one or more modified structures are created which have the same compositional formula as the deduced compositional formula, by combining as previously described. The structures created hereby are listed as candidate structures of the unknown substance. Next, a fragment ion peak which is expected to appear if an MS$^n$ analysis of the candidate structures is performed is deduced, and then the candidate structures are ranked in the order in which they explain the fragment ion obtained by the MS$^n$ analysis of the unknown substance based on the information of the expected fragment ion peak. Accordingly, by the method according to the second aspect of the present invention, it is possible to deduce the structure of an unknown substance easier, even if a common fragment ion peak which exists both in the unknown substance and in a known substance cannot be found as in the case described earlier, it is possible to deduce the structure of the unknown substance.

When deducing the structure of an unknown substance by the method of analyzing mass analysis data according to the present invention, it is necessary to prepare a database having information on known substances which have similar structures to that of the unknown substance. For example, when an MS$^n$ analysis of a substance whose structure is unknown is performed and a certain known substance is detected as a substance similar to the unknown substance by performing a pattern matching operation using such a database, it is preferable to practice the method according to the second aspect of the present invention using the result of an MS$^n$ analysis of an unknown substance and information on substances similar to the unknown substance which are stored in the database. Also, it is preferable to practice the method according to the second aspect of the present invention when performing an MS$^n$ analysis of a sample which has various components, then selecting a component similar to a known substance included in the sample, and analyzing the structure of the component. This kind of analysis includes, for example, quantitative determination and/or structural analysis of metabolites in the pharmacokinetics studies, and identification of analogous impurities of by-products and/or decomposition products in the synthesis of pharmaceutical compounds.

EXPLANATION OF NUMERALS

10 . . . Data Analyzing Apparatus
11 . . . Central Control Unit
12 . . . Spectral Data Creator
13 . . . Analyzing Processor
14 . . . Measured Data Memory Unit
15 . . . Reference Data Memory Unit
16 . . . Structural Change Pattern Memory Unit
30 . . . LC/MS
40 . . . Input Unit
50 . . . Monitor
61 . . . Measured Data Retriever
62 . . . Partial Structure Retriever
63 . . . Second Partial Structure Retriever
64 . . . Common Peak Detector
65 . . . Partial Structure Determining Means 66 . . . Mass-To-Charge Ratio Difference Calculator
67 . . . Common Mass-To-Charge Ratio Difference Detector
68 . . . Second Partial Structure Determiner
69 . . . Compositional Formula Deducer
70 . . . Candidate Structure Creator
71 . . . Fragment Ion Deducer
72 . . . Ranking Means

DETAILED DESCRIPTION OF PREFERRED EMBODIMENTS

An embodiment of the apparatus for analyzing mass analysis data (data analyzing apparatus), which carries out an analysis by a method of analyzing mass analysis data according to the present invention, is described with reference to the drawings. Although the result of an analysis by a liquid chromatograph-mass spectrometer is used in this embodiment, other types of chromatograph-mass spectrometers such as a gas chromatograph-mass spectrometer, or a mass spectrometer with direct sample injection can alternatively be used.

Figure 1:
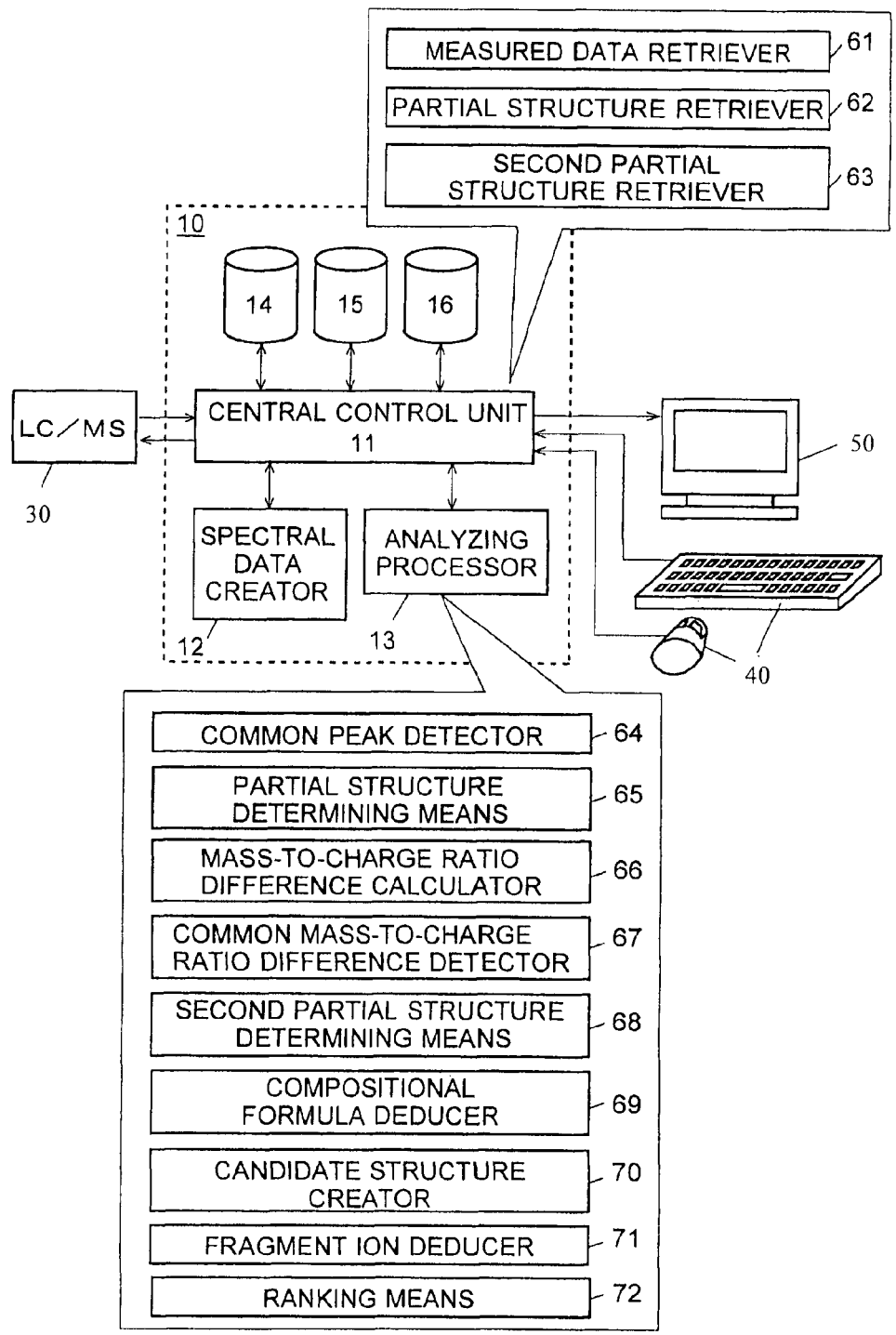
FIG. 1 is a schematic diagram of the apparatus for data analyzing apparatus according to an embodiment of the present invention.

FIG. 1 is a schematic diagram of the apparatus for the data analyzing apparatus 10 of the present embodiment. The data analyzing apparatus 10 processes detected data delivered from LC/MS 30. The data analyzing apparatus 10 contains a central control unit 11, a spectral data creator 12, an analyzing processor 13, a measured data memory unit 14, a reference data memory unit 15, and a structural change pattern memory unit 16. The measured data memory unit 14, the reference data memory unit 15, and the structural change pattern memory unit 16 are connected to the central control unit 11. An input unit 40 and a monitor 50 are connected to the central control unit 11. The central control unit 11 has functions to control the operation of the LC/MS 30.

The central control unit 11, the spectral data creator 12, and the analyzing processor 13 are realized by a CPU (Central Processing Unit) running a specific application program.

The central control unit 11 contains a measured data retriever 61, a partial structure retriever 62, and a second partial structure retriever 63, all of which are realized by the CPU running the specific program. The analyzing processor 13 contains a common peak detector 64, a partial structure determining means 65, a mass-to-charge ratio difference calculator 66, a common mass-to-charge ratio difference detector 67, a second partial structure determining means 68, a compositional formula deducer 69, a candidate structure creator 70, a fragment ion deducer 71, and a ranking means 72, all of which are also realized by the CPU running the specific program.

The measured data memory unit 14 is a read/write storage device such as a hard disk drive or magnetooptic (MO) disc drive. The reference data memory unit 15 and the structural change pattern memory unit 16 can be a hard disk drive, or read-only device such as a CD-ROM drive if no data is to be written to them. In the reference data memory unit 15, various data relevant to compounds (e.g. structural formulas, compositional formulas, spectral data at each step of an $MS^n$ analysis, and information on partial structures which correspond to each of the fragment ion peaks in the spectral data) are stored. An operator can specify a compound from the stored compounds by operating the input unit 40. In the structural change pattern memory unit 16, information on known structural change patterns (e.g. patterns of substitutions, additions, and desorptions of substituents) are stored. Although the measured data memory unit 14, the reference data memory unit 15, and the structural change pattern memory 16 are shown independently in FIG. 1, it is possible to use a single storage device, such as a hard disk drive, which has logical segments.

The input unit 40 includes a keyboard and/or mouse, and the monitor 50 includes a cathode ray tube (CRT) and/or printer.

The data analyzing apparatus 10 can be realized as an operating/analyzing unit for LC/MS only, or as a general computer system such as a personal computer in which a program for performing the analysis method of the present invention is installed.

The LC/MS 30 consists of a liquid chromatograph having a column for temporally separating a mixed sample, and a mass spectrometer capable of an $MS^n$ (at least $MS^2$) analysis. As a mass spectrometer of this kind, it is possible, for example, to use a triple quadrupole mass spectrometer or an ion trap mass spectrometer. Sample components eluted from the column of the chromatograph are sequentially ionized by the mass spectrometer and then analyzed using the $MS^n$ analysis. Ions having a proper mass-to-charge ratio are selected as precursor ions automatically from ions originating from each of the sample components. The precursor ions are dissociated into fragment ions, and the fragment ions are mass-separated and detected. The selection, dissociation, and detection of the ions can be repeated, if necessary, multiple times.

While the sample is being measured, detected data (digitized detected signals) regarding electric current according to the number of ions detected at each mass-to-charge ratio is sent from the LC/MS 30 to the data analyzing apparatus 10. The spectral data creator 12 calculates the spectral data, in which a mass-to-charge ratio and peak intensity at the mass-to-charge ratio (relative signal intensity) are paired, by processing the detected data in accordance with a predetermined algorithm. The spectral data is then stored in the measured data memory unit 14. Also, a total ion chromatogram (TIC) is produced based on the spectral data obtained by an $MS^1$ analysis in which no dissociating operation is performed, and the total ion chromatogram is stored in the measured data memory unit 14.

Next, an analysis process after the sample is measured is described. First, an $MS^n$ analysis of a mixed sample is performed, and an unknown substance is selected which is similar to a certain known substance using the analysis data. And then, a structural analysis of the unknown substance is carried out using the method of analyzing mass analysis data according to the present invention.

First, the central control unit 11 retrieves spectral data (spectral data obtained at each step of the $MS^n$ analysis) which corresponds to each peak on the TIC from the measured data memory unit 14. The central control unit 11 also retrieves spectral data of the target component specified by the operator from the reference data memory unit 15. The central control unit 11 then sends the spectral data and the spectral data of the target component to the analyzing processor 13.

Based on the spectral data, the analyzing processor 13 detects parameters for the multivariable analysis, which is to be described later, and creates a table of the parameters. The preferable parameters for the multivariable analysis are, for example, at least one of the following; (1) a mass-to-charge ratio of a fragment ion at each dissociating step of an $MS^n$ analysis, (2) a difference between a mass-to-charge ratio of a fragment ion and a mass-to-charge ratio of the precursor ion at each dissociating step of an $MS^n$ analysis, (3) a difference between a mass-to-charge ratio of a fragment ion at each dissociating step of an $MS^n$ analysis and a mass-to-charge ratio of a fragment ion or a precursor ion at the previous step, which were original ions of the fragment ion, (4) an isotopic distribution pattern of a precursor ion.

Next, the analyzing processor 13 executes the multivariable analysis based on the table, and evaluates one or more similarity values between each of the sample components and the target component. As a method for the multivariable analysis, it is possible to use Hierarchical Cluster Analysis (HCA), Principal Component Analysis (PCA), or Partial Least Squares (PLS).

Subsequently, the result of the multivariable analysis executed by the analyzing processor 13 is shown on the monitor 50, and candidates for the similar component are selected based on the result. At this point, the operator looks at the results shown on the monitor 50 and selects a candidate for the similar component. Or, instead, the data analyzing apparatus 10 automatically selects a component which has a higher similarity value than a predetermined threshold, and displays the component on the monitor 50.

Figure 2:
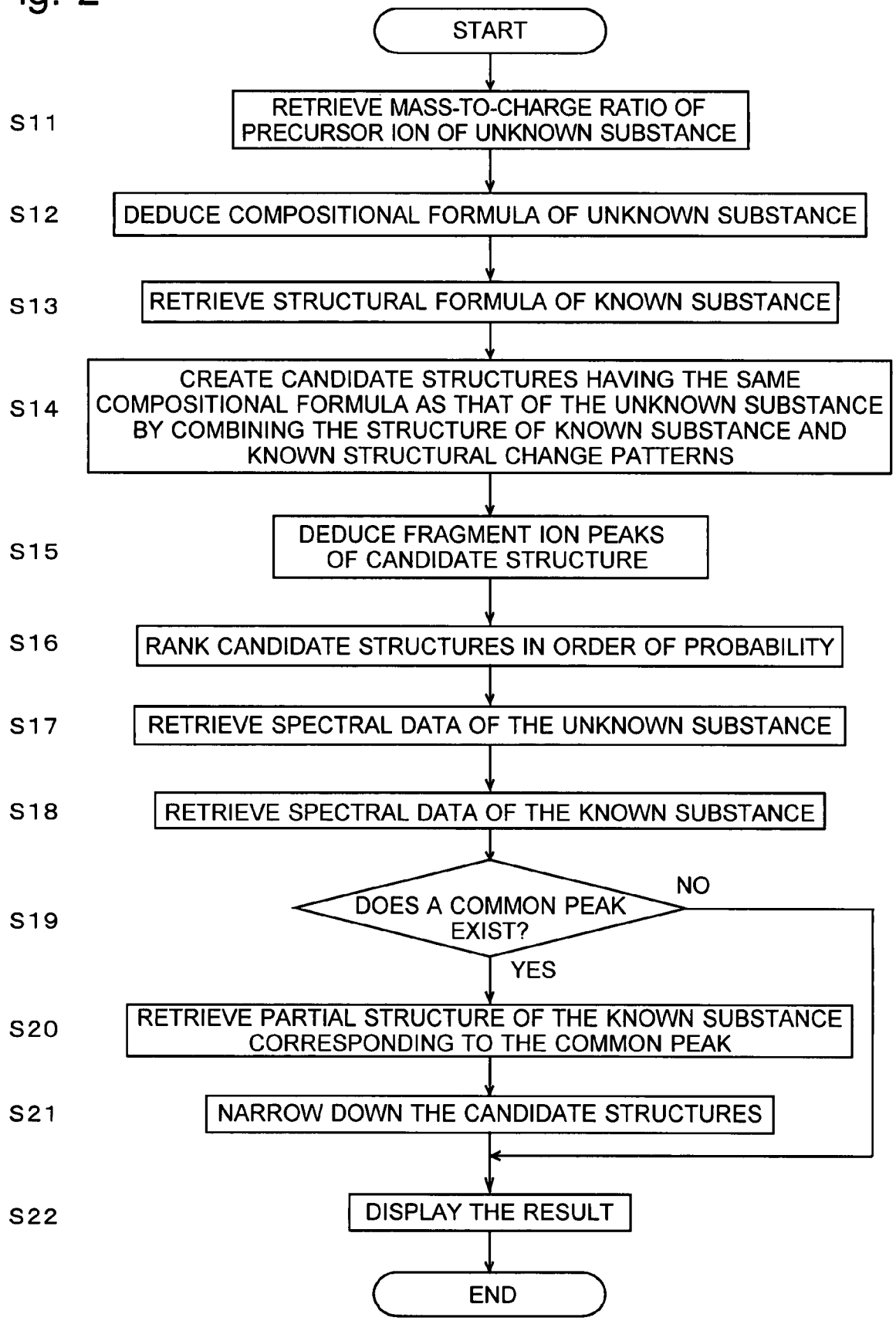
FIG. 2 is a flow chart showing an example of the characteristic steps of the analysis process for analyzing a structure of an unknown substance according to the present embodiment.

As just described, the $MS^n$ analysis data of the unknown substance and information on the known substance which is similar to the unknown substance are obtained. Next, a process for deducing the structure of the unknown substance which is selected as a candidate based on the analysis data and the information is described with reference to the flow chart shown in FIG. 2.

In the first step, the central control unit 11 retrieves a mass-to-charge ratio of a precursor ion originating from an unknown substance (or a candidate for the similar component) to be analyzed from the measured data memory unit 14, and transfers the mass-to-charge ratio to the analyzing processor 13 (Step S11). The analyzing processor 13 (the compositional formula deducer 69) deduces a compositional formula using the mass-to-charge ratio of the precursor ion (Step S12). Then, the central control unit 11 retrieves the structural formula of the known substance from the reference data memory unit 15 and transfers it to the analyzing processor 13 (Step S13). The analyzing processor 13 (the candidate structure creator 70) refers to the structural change pattern memory unit 16, and creates candidate structures for obtaining the same compositional formula as the compositional formula deduced in step S13, by combining the structure of the known substance and the known structural change patterns (Step S14).

In the next step, the analyzing processor 13 (the fragment ion deducer 71) deduces fragment ion peaks which are expected to appear by an $MS^2$ analysis of each candidate structure obtained in Step S14 (Step S15). The analyzing processor 13 (the ranking means 72) then ranks the candidate structures in descending order of the probability of the structure of the unknown substance by taking into account the mass-to-charge ratios and peak heights of each of the fragment ion peaks deduced in Step S15 (Step S16).

Next, the central control unit 11 (the measured data retriever 61) retrieves the $MS^2$ spectrum of the known substance from the reference data memory unit 15 as well as the $MS^2$ spectrum of the unknown substance from the measured data memory unit 14, and transfers them to the analyzing processor 13 (Step S17, S18). The analyzing processor 13 (the common peak detector 64) detects a fragment ion peak which exists in both of the $MS^2$ spectra received in Steps S17 and S18, by comparing these spectra (Step S19). If a common peak is found in Step S19, it is probable that a partial structure corresponding to the fragment ion peak is included in the unknown substance.

Figure 3A:
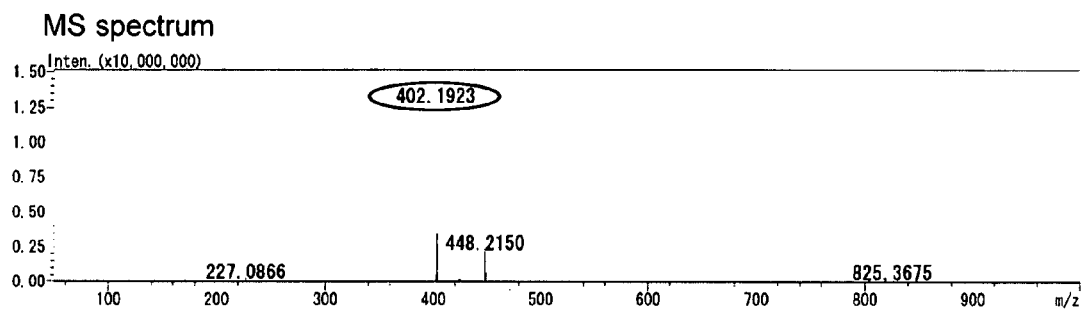
FIG. 3A is an example of MS spectrum of a known substance.
Figure 3B:
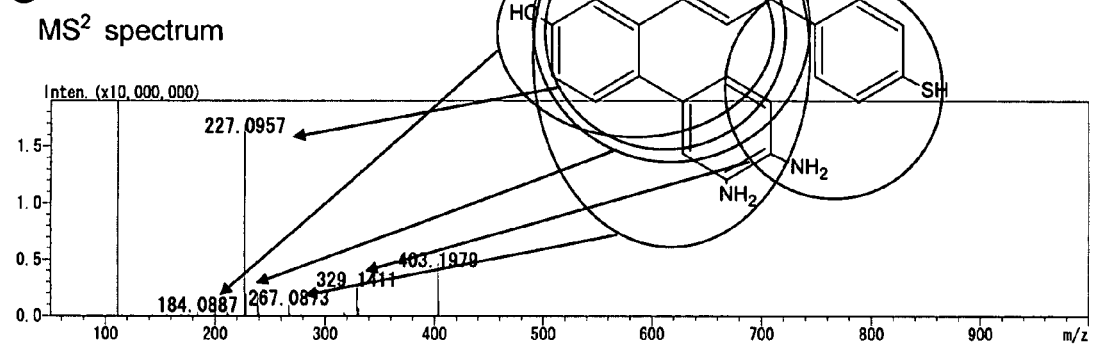
FIG. 3B is an example of MS$^2$ spectrum of a known substance.
Figure 4A:
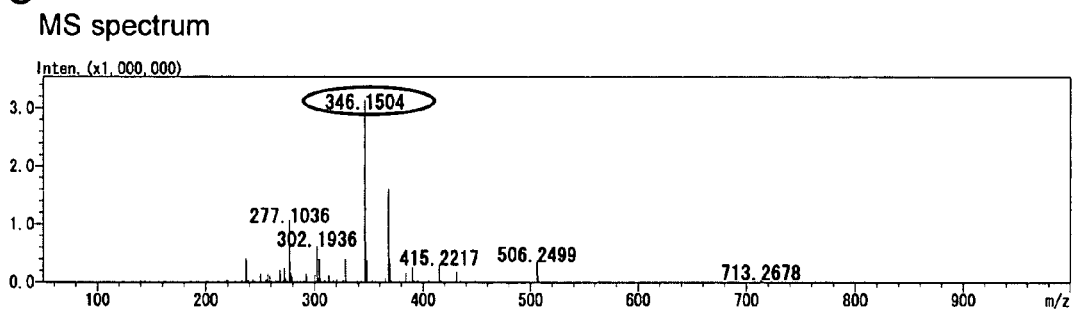
FIG. 4A is an example of MS spectrum of an unknown substance.
Figure 4B:
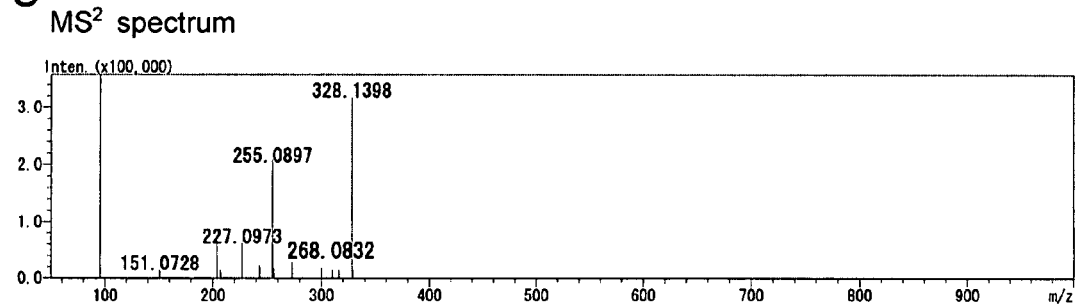
FIG. 4B is an example of MS$^2$ spectrum of an unknown substance.

A concrete example is next described: an MS spectrum shown in FIG. 3A and $MS^2$ spectrum (obtained by dissociating the m/z=402.1923 peak on the MS spectrum) shown in FIG. 3B are stored in the reference data memory unit 15. The known substance has a molecular structure as shown by the structural formula in FIG. 3B, and each fragment ion peak on the $MS^2$ spectrum is derived from each circled part of the structural formula. Information on these molecular structures and the partial structures are also stored in the reference data memory unit 15. When the MS spectrum of the unknown substance is a spectrum shown in FIG. 4A, and the $MS^2$ spectrum is a spectrum shown in FIG. 4B, by comparing these spectra, it is found that the m/z=227 peak and the m/z=268 peak are common to the MS spectrum and the $MS^2$ spectrum. Consequently, it is probable that the unknown substance has partial structures which correspond to the m/z=227 and m/z=268 fragment ion peaks as shown in FIG. 3B.

If a common peak is found in Step S19, the central control unit 11 (the partial structure retriever 62) retrieves information on the partial structure of the known substance which corresponds to the common peak from the reference data memory unit 15 and transfers it to the analyzing processor 13 (Step S20). The analyzing processor 13 (the partial structure determining means 65) narrows down the candidate structures obtained in Step S16 by using the information on the partial structure (Step S21), and the result of the narrowing down process is displayed on the monitor 50 in the order of probability (Step S22). When no common peak is found in Step S19, no narrowing down process is performed and the result of Step S16 is displayed on the monitor 50 in the order of probability (Step S22).

The method of analyzing mass analysis data according to the invention can be performed not only to deduce a structure based on the steps of the flow chart as described before and shown in FIG. 2, but also only to find a fragment ion peak which is common to the unknown substance and the known substance, and deduce a partial structure of the unknown substance (Steps S17 through S20). For example, another (second) multivariable analysis of the parameters regarding a plurality of unknown substances which are deduced as candidates regarding the similar component to a certain known substance by the multivariable analysis performed earlier and the known substance is performed. Based on the result of the second multivariable analysis, the candidates for the similar component are grouped by their characteristics. Then, a common peak is searched for each group of the unknown substances in such a manner as described earlier; that is, peaks which exist both in the unknown substances of each group and in the known substance are detected. Since the detected peak shows that there exists a common structure between the unknown substance belonging to the group and the known substance, it is possible to specify the common structure based on the partial structure of the known substance corresponding to the peak.

It should be noted that the embodiment described thus far is a mere example, which can be changed, modified or expanded within the sprit of the present invention. For example, although in the embodiment described thus far, the analysis is based on data of $MS^2$ analysis (MS/MS analysis), the present invention can be applied for the analysis based on data of $MS^n$ analysis having two or more dissociating steps.

In the embodiment described earlier, a fragment ion peak which is common to the known substance and the unknown substance is searched and based on the search result, the candidate structures are narrowed down in Steps S19 through S21. However, it is possible to use a difference value between the mass-to-charge ratio of each fragment ion (md) and the mass-to-charge ratio of a precursor ion (mp) alternatively. In this case, as information on the known substance, spectral data of an $MS^2$ analysis, information on the partial structure corresponding to each fragment ion peak in the spectral data, the difference value between the mass-to-charge ratios (mp– md), and information on the partial structure corresponding to the different value of the mass-to-charge ratio are stored preliminarily in the reference data memory unit 15. Since a difference value between the mass-to-charge ratios (mp−md) corresponds to an element desorbed by the dissociation of a precursor ion, the difference value is attributable to a partial structure of the known substance as in the case of a fragment ion peak. Therefore, if a difference value between the mass-to-charge ratios (mp−md) is calculated by the mass-to-charge ratio difference calculator 66 regarding each fragment ion peak in an $MS^n$ spectrum based on a result of an analysis of an unknown substance, and a difference value which is common to the unknown substance and the known substance is detected by the common mass-to-charge ratio difference detector 67. Since it is possible to deduce that a partial structure of the known substance corresponding to the difference value between the mass-to-charge ratios is included in the unknown substance, the second partial structure retriever 63 retrieves the partial structure of the known substance from the reference data memory unit 15 and then transfers it to the second partial structure determining means 68 which determines the partial structure as the structure of the unknown substance, for example, by executing a narrowing down process. When using a result of an $MS^n$ analysis having two or more dissociating steps, it is possible to use information on a difference value between a mass-to-charge ratio of a fragment ion at each dissociating step of the $MS^n$ analysis and a mass-to-charge ratio of a fragment ion or a precursor ion at the previous step, which were original ions of the fragment ion, in addition to the difference value between the mass-to-charge ratio of the precursor ion and the mass-to-charge ratio of the fragment ion at each step.

What is claimed is:

1. A method of analyzing mass analysis data for deducing a structure of an unknown substance, based on a result of an $MS^n$ analysis in which a precursor ion originating from the unknown substance is dissociated into fragment ions by (n−1) steps (where n≧2) and then the fragment ions are subjected to a mass-analyzing process, the method comprising steps of:
    a) comparing a mass spectrum of the unknown substance obtained by the $MS^n$ analysis and a mass spectrum of a known substance similar to the unknown substance and then detecting a common fragment ion peak existing in both of the mass spectra;
    b) identifying a partial structure of the known substance, the partial structure corresponding to the common fragment ion peak;
    c) determining the partial structure as a partial structure of the unknown substance;
    d) calculating a difference value between a mass-to-charge ratio of a fragment ion and a mass-to-charge ratio of a precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;
    e) comparing the difference value between the mass-to-charge ratios regarding the unknown substance and the difference value preliminarily calculated between the mass-to-charge ratios regarding the known substance, and then detecting a common difference value;
    f) identifying a partial structure of the known substance, the partial structure corresponding to the common difference value between the mass-to-charge ratios detected in step e); and
    g) determining the partial structure as a partial structure of the unknown substance.

2. A method of analyzing mass analysis data for deducing a structure of an unknown substance, based on a result of an $MS^n$ analysis in which a precursor ion originating from the unknown substance is dissociated into fragment ions by (n−1) steps (where n≧2) and then the fragment ions are subjected to a mass-analyzing process, the method comprising steps of:
    a) comparing a mass spectrum of the unknown substance obtained by the $MS^n$ analysis and a mass spectrum of a known substance similar to the unknown substance and then detecting a common fragment ion peak existing in both of the mass spectra;
    b) identifying a partial structure of the known substance, the partial structure corresponding to the common fragment ion peak;
    c) determining the partial structure as a partial structure of the unknown substance;
    d) calculating a difference value between a mass-to-charge ratio of a fragment ion and a mass-to-charge ratio of a precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;
    e) comparing the difference value between the mass-to-charge ratios regarding the unknown substance and the difference value preliminarily calculated between the mass-to-charge ratios regarding the known substance, and then detecting a common difference value;
    f) identifying a partial structure of the known substance, the partial structure corresponding to the common difference value between the mass-to-charge ratios detected in step e);
    g) determining the partial structure as a partial structure of the unknown substance;
    h) deducing a compositional formula of a precursor ion originating from the unknown substance based on the mass-to-charge ratio of the precursor ion;
    i) creating candidate structures for obtaining a same compositional formula as the compositional formula deduced in step h), by combining the structure of the known substance and known structural change patterns;
    j) deducing a fragment ion peak obtained by an $MS^n$ analysis of the candidate structures; and
    k) ranking the candidate structures in descending order of a probability of the structure of the unknown substance by comparing the fragment ion peak deduced in step j) and a fragment ion peak obtained by an $MS^n$ analysis of the unknown substance.

3. A method of analyzing mass analysis data for deducing a structure of an unknown substance, based on a result of an $MS^n$ analysis in which a precursor ion originating from the unknown substance is dissociated into fragment ions by (n−1) steps (where n≧2) and then the fragment ions are subjected to a mass-analyzing process, the method comprising steps of:
    a) comparing a mass spectrum of the unknown substance obtained by the $MS^n$ analysis and a mass spectrum of a known substance similar to the unknown substance and then detecting a common fragment ion peak existing in both of the mass spectra;
    b) identifying a partial structure of the known substance, the partial structure corresponding to the common fragment ion peak;

c) determining the partial structure as a partial structure of the unknown substance;

d) deducing a compositional formula of a precursor ion originating from the unknown substance based on a mass-to-charge ratio of the precursor ion;

e) creating candidate structures for obtaining a same compositional formula as the compositional formula deduced in step h), by combining the structure of the known substance and known structural change patterns;

f) deducing a fragment ion peak obtained by an $MS^n$ analysis of the candidate structures; and g) ranking the candidate structures in descending order of a probability of the structure of the unknown substance by comparing the fragment ion peak deduced in step j) and a fragment ion peak obtained by an $MS^n$ analysis of the unknown substance.

4. An apparatus for analyzing mass analysis data for deducing a structure of an unknown substance, based on a result of an $MS^n$ analysis in which a precursor ion originating from the unknown substance is dissociated into fragment ions by (n−1) steps (where $n \geq 2$) and then the fragment ions are subjected to a mass-analyzing process, the apparatus comprising:

a) a measured data retriever for retrieving a mass spectrum of the unknown substance obtained by the $MS^n$ analysis;

b) a memory unit for storing (i) a mass spectrum of a known substance similar to the unknown substance, (ii) partial structure information of the known substance, the partial structure corresponding to a detected fragment ion peak on the mass spectrum, (iii) a difference value between a mass-to-charge ratio of a fragment ion and a mass-to-charge ratio of a precursor ion at each dissociating step of an $MS^n$ analysis of the known substance, and/or (iv) a difference value between a mass-to-charge ratio of a fragment ion at each dissociating step of an $MS^n$ analysis and a mass-to-charge ratio of a fragment ion or a precursor ion at the previous step, which were original ions of the fragment ion;

c) a common peak detector for comparing the mass spectrum of the unknown substance obtained by the measured data retriever and the mass spectrum of a known substance retrieved from the memory unit, and then detecting a common fragment ion peak existing in both of the mass spectra;

d) a partial structure retriever for retrieving the partial structure information corresponding to the common fragment ion peak from the memory unit;

e) a partial structure determining means for determining the partial structure as a partial structure of the unknown substance;

f) a mass-to-charge ratio difference calculator for calculating a difference value between a mass-to-charge ratio of a fragment ion and a mass-to-charge ratio of a precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;

g) a common mass-to-charge ratio difference detector for comparing the difference value between the mass-to-charge ratios regarding the unknown substance obtained by the mass-to-charge ratio difference calculator and the difference value preliminarily calculated between the mass-to-charge ratios regarding the known substance retrieved from the memory unit, and then detecting a common difference value;

h) a second partial structure retriever for retrieving the partial structure of the known substance from the memory unit, the partial structure corresponding to the common difference value; and i) a second partial structure determining means for determining the partial structure as a structure of the unknown substance.

5. An apparatus for analyzing mass analysis data for deducing a structure of an unknown substance, based on a result of an $MS^n$ analysis in which a precursor ion originating from the unknown substance is dissociated into fragment ions by (n−1) steps (where $n \geq 2$) and then the fragment ions are subjected to a mass-analyzing process, the apparatus comprising:

a) a measured data retriever for retrieving a mass spectrum of the unknown substance obtained by the $MS^n$ analysis;

b) a memory unit for storing (i) a mass spectrum of a known substance similar to the unknown substance, (ii) partial structure information of the known substance, the partial structure corresponding to a detected fragment ion peak on the mass spectrum, (iii) a difference value between a mass-to-charge ratio of a fragment ion and a mass-to-charge ratio of a precursor ion at each dissociating step of an $MS^n$ analysis of the known substance, and/or (iv) a difference value between a mass-to-charge ratio of a fragment ion at each dissociating step of an $MS^n$ analysis and a mass-to-charge ratio of a fragment ion or a precursor ion at the previous step, which were original ions of the fragment ion;

c) a common peak detector for comparing the mass spectrum of the unknown substance obtained by the measured data retriever and the mass spectrum of a known substance retrieved from the memory unit, and then detecting a common fragment ion peak existing in both of the mass spectra;

d) a partial structure retriever for retrieving the partial structure information corresponding to the common fragment ion peak from the memory unit;

e) a partial structure determining means for determining the partial structure as a partial structure of the unknown substance;

f) a mass-to-charge ratio difference calculator for calculating a difference value between a mass-to-charge ratio of a fragment ion and a mass-to-charge ratio of the precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;

g) a common mass-to-charge ratio difference detector for comparing the difference value between the mass-to-charge ratios regarding the unknown substance obtained by the mass-to-charge ratio difference calculator and the difference value preliminarily calculated between the mass-to-charge ratios regarding the known substance retrieved from the memory unit, and then detecting a common difference value;

h) a second partial structure retriever for retrieving the partial structure of the known substance from the memory unit, the partial structure corresponding to the common difference value;

i) a second partial structure determining means for determining the partial structure as a structure of the unknown substance;

j) a compositional formula deducer for deducing a compositional formula of a precursor ion originating from the unknown substance based on the mass-to-charge ratio of the precursor ion;

k) a candidate structure creator for creating candidate structures for obtaining a same compositional formula as the compositional formula deduced by the compositional formula deducer, by combining the structure of the known substance and known structural change patterns;

l) a fragment ion deducer for deducing a fragment ion peak obtained by an $MS^n$ analysis of the candidate structures; and m) a ranking means for ranking the candidate structures in descending order of a probability of the structure of the unknown substance by comparing the fragment ion peak and a fragment ion peak obtained by an $MS^n$ analysis of the unknown substance.

6. An apparatus for analyzing mass analysis data for deducing a structure of an unknown substance, based on a result of an $MS^n$ analysis in which a precursor ion originating from the unknown substance is dissociated into fragment ions by (n−1) steps (where n≧2) and then the fragment ions are subjected to a mass-analyzing process, the apparatus comprising:

a) a measured data retriever for retrieving a mass spectrum of the unknown substance obtained by the $MS^n$ analysis;

b) a memory unit for storing (i) a mass spectrum of a known substance similar to the unknown substance and (ii) partial structure information of the known substance, the partial structure corresponding to a detected fragment ion peak on the mass spectrum;

c) a common peak detector for comparing the mass spectrum of the unknown substance obtained by the measured data retriever and the mass spectrum of a known substance retrieved from the memory unit, and then detecting a common fragment ion peak existing in both of the mass spectra;

d) a partial structure retriever for retrieving the partial structure information corresponding to the common fragment ion peak from the memory unit;

e) a partial structure determining means for determining the partial structure as a partial structure of the unknown substance;

f) a compositional formula deducer for deducing a compositional formula of a precursor ion originating from the unknown substance based on a mass-to-charge ratio of the precursor ion;

g) a candidate structure creator for creating candidate structures for obtaining a same compositional formula as the compositional formula deduced by the compositional formula deducer, by combining the structure of the known substance and known structural change patterns;

h) a fragment ion deducer for deducing a fragment ion peak obtained by an $MS^n$ analysis of the candidate structures; and i) a ranking means for ranking the candidate structures in descending order of a probability of the structure of the unknown substance by comparing the fragment ion peak and a fragment ion peak obtained by an $MS^n$ analysis of the unknown substance.

7. A mass analysis data analyzing program for operating a computer, which includes a memory unit for storing (i) a mass spectrum of a known substance similar to an unknown substance, (ii) partial structure information of the known substance, the partial structure corresponding to a detected fragment ion peak on the mass spectrum, (iii) a difference value between a mass-to-charge ratio of a fragment ion and a mass-to-charge ratio of a precursor ion at each dissociating step of an $MS^n$ analysis of the known substance, and/or (iv) a difference value between a mass-to-charge ratio of a fragment ion at each dissociating step of an $MS^n$ analysis and a mass-to-charge ratio of a fragment ion or a precursor ion at the previous step, which were original ions of the fragment ion, as an apparatus for analyzing mass analysis data for deducing a structure of the unknown substance, based on a result of an $MS^n$ analysis in which a precursor ion originating from the unknown substance is dissociated into fragment ions by (n−1) steps (where n≧2) and then the fragment ions are subjected to a mass-analyzing process, the apparatus comprising:

a) a measured data retriever for retrieving a mass spectrum of the unknown substance obtained by the $MS^n$ analysis;

b) a common peak detector for comparing the mass spectrum of the unknown substance obtained by the measured data retriever and the mass spectrum of a known substance retrieved from the memory unit, and then detecting a common fragment ion peak existing in both of the mass spectra;

c) a partial structure retriever for retrieving the partial structure information corresponding to the common fragment ion peak from the memory unit;

d) a partial structure determining means for determining the partial structure as a partial structure of the unknown substance;

e) a mass-to-charge ratio difference calculator for calculating a difference value between a mass-to-charge ratio of a fragment ion and a mass-to-charge ratio of a precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;

f) a common mass-to-charge ratio difference detector for comparing the difference value between the mass-to-charge ratios regarding the unknown substance obtained by the mass-to-charge ratio difference calculator and the difference value preliminarily calculated between the mass-to-charge ratios regarding the known substance retrieved from the memory unit, and then detecting a common difference value;

g) a second partial structure retriever for retrieving the partial structure of the known substance from the memory unit, the partial structure corresponding to the common difference value; and h) a second partial structure determining means for determining the partial structure as a structure of the unknown substance.

8. A mass analysis data analyzing program for operating a computer, which includes a memory unit for storing (i) a mass spectrum of a known substance similar to an unknown substance, (ii) partial structure information of the known substance, the partial structure corresponding to a detected fragment ion peak on the mass spectrum, (iii) a difference value between a mass-to-charge ratio of a fragment ion and a mass-to-charge ratio of a precursor ion at each dissociating step of an $MS^n$ analysis of the known substance, and/or (iv) a difference value between a mass-to-charge ratio of a fragment ion at each dissociating step of an $MS^n$ analysis and a mass-to-charge ratio of a fragment ion or a precursor ion at the previous step, which were original ions of the fragment ion, as an apparatus for analyzing mass analysis data for deducing a structure of the unknown substance, based on a result of an $MS^n$ analysis in which a precursor ion originating from the unknown substance is dissociated into fragment ions by (n−1) steps (where n≧2) and then the fragment ions are subjected to a mass-analyzing process, the apparatus comprising:

a) a measured data retriever for retrieving a mass spectrum of the unknown substance obtained by the $MS^n$ analysis;

b) a common peak detector for comparing the mass spectrum of the unknown substance obtained by the measured data retriever and the mass spectrum of a known substance retrieved from the memory unit, and then detecting a common fragment ion peak existing in both of the mass spectra;

c) a partial structure retriever for retrieving the partial structure information corresponding to the common fragment ion peak from the memory unit;

d) a partial structure determining means for determining the partial structure as a partial structure of the unknown substance;

e) a mass-to-charge ratio difference calculator for calculating a difference value between a mass-to-charge ratio of a fragment ion and a mass-to-charge ratio of the precursor ion at each dissociating step of an $MS^n$ analysis of the unknown substance, and/or a difference value between a mass-to-charge ratio of a fragment ion at each dissociating step of the $MS^n$ analysis and a mass-to-charge ratio of a fragment ion or a precursor ion at the previous step, which were original ions of the fragment ion;

f) a common mass-to-charge ratio difference detector for comparing the difference value between the mass-to-charge ratios regarding the unknown substance obtained by the mass-to-charge ratio difference calculator and the difference value preliminarily calculated between the mass-to-charge ratios regarding the known substance retrieved from the memory unit, and then detecting a common difference value;

g) a second partial structure retriever for retrieving the partial structure of the known substance from the memory unit, the partial structure corresponding to the common difference value;

h) a second partial structure determining means for determining the partial structure as a structure of the unknown substance;

i) a compositional formula deducer for deducing a compositional formula of a precursor ion originating from the unknown substance based on the mass-to-charge ratio of the precursor ion;

j) a candidate structure creator for creating candidate structures for obtaining a same compositional formula as the compositional formula deduced by the compositional formula deducer, by combining the structure of the known substance and known structural change patterns;

k) a fragment ion deducer for deducing a fragment ion peak obtained by an $MS^n$ analysis of the candidate structures; and l) a ranking means for ranking the candidate structures in descending order of a probability of the structure of the unknown substance by comparing the fragment ion peak and a fragment ion peak obtained by an $MS^n$ analysis of the unknown substance.

9. A mass analysis data analyzing program for operating a computer, which includes a memory unit for storing (i) a mass spectrum of a known substance similar to an unknown substance and (ii) partial structure information of the known substance, the partial structure corresponding to a detected fragment ion peak on the mass spectrum, the apparatus comprising:

a) a measured data retriever for retrieving a mass spectrum of the unknown substance obtained by the $MS^n$ analysis;

b) a common peak detector for comparing the mass spectrum of the unknown substance obtained by the measured data retriever and the mass spectrum of a known substance retrieved from the memory unit, and then detecting a common fragment ion peak existing in both of the mass spectra;

c) a partial structure retriever for retrieving the partial structure information corresponding to the common fragment ion peak from the memory unit;

d) a partial structure determining means for determining the partial structure as a partial structure of the unknown substance;

e) a compositional formula deducer for deducing a compositional formula of a precursor ion originating from the unknown substance based on a mass-to-charge ratio of the precursor ion;

f) a candidate structure creator for creating candidate structures for obtaining a same compositional formula as the compositional formula deduced by the compositional formula deducer, by combining the structure of the known substance and known structural change patterns;

g) a fragment ion deducer for deducing a fragment ion peak obtained by an $MS^n$ analysis of the candidate structures; and h) a ranking means for ranking the candidate structures in descending order of a probability of the structure of the unknown substance by comparing the fragment ion peak and a fragment ion peak obtained by an $MS^n$ analysis of the unknown substance.

* * * * *